United States Patent [19]

Cowfer et al.

[11] 4,226,798

[45] Oct. 7, 1980

[54] METHOD OF SELECTING OPERATION OF A FLUID-BED REACTOR AND APPARATUS FOR DOING SO

[75] Inventors: Joseph A. Cowfer, Medina; Dane E. Jablonski, Broadview Heights; Ronald M. Kovach, Avon Lake; Angelo J. Magistro, Brecksville, all of Ohio

[73] Assignee: The B. F. Goodrich Company, Akron, Ohio

[21] Appl. No.: 949,170

[22] Filed: Oct. 6, 1978

[51] Int. Cl.³ ............... C07C 120/14; C07C 45/04; C07C 17/15; G05D 24/00

[52] U.S. Cl. ............... 260/465.3; 23/230 A; 73/54; 137/4; 137/92; 422/110; 422/111; 422/145; 423/DIG. 16; 568/478; 568/479; 570/243

[58] Field of Search ............ 423/DIG. 16; 23/230 A; 422/110, 111, 145; 260/465.3, 604 R, 664, 659 R, 659 A, 662 A

[56] References Cited

U.S. PATENT DOCUMENTS 3,488,398 1/1970 Harpring et al. ............... 260/659 A

OTHER PUBLICATIONS

Ashwin, et al., C.A., 56 (1962), 12696g.
Cergel, et al., C.A., 74 (1971), 143636a.
Ashwin, et al., J. Sci. Instruments, 37, (1960), pp. 480-485.
Matheson, et al., Ind. Eng. Chem., 41, (1949), pp. 1099-1104.

Primary Examiner—Joseph Paul Brust
Attorney, Agent, or Firm—Alfred D. Lobo; J. Hughes Powell, Jr.

[57] ABSTRACT

A method is disclosed for using a pendulum viscometer having damped torsional oscillations, in a laboratory catalytic fluid-bed reactor, to monitor a propensity to stick which is exhibited by certain supported catalysts. A fluid-bed of such catalysts has been found to become suddenly more sticky just before a point at which a change in pressure drop across the fluid-bed can be measured due to a process "upset". At this point ("the inversion point"), the upset is usually irremediable. The method includes correlating data on catalyst stickiness from a laboratory reactor operating at atmospheric pressure, with an expected level of catalyst stickiness in a commercial reactor operating at elevated pressure.

A pendulum viscometer and related auxiliary apparatus is disclosed for magnetically and electrically measuring and recording the rate at which the pendulum's torsional oscillations are damped. Frequent measurements are made during normal operation of the fluid-bed to determine its stickiness (as evidenced by the rate at which the pendulum's torsional oscillations are damped) relative to the stickiness at the inversion point. Operation of the fluid-bed under conditions for which measured rates of damping are predeterminedly lower than the rate near the inversion point, assures operation of the fluid-bed reactor at maximum efficiency.

20 Claims, 5 Drawing Figures $\ln A = -kt + \ln A_0$
SLOPE = $-k$

METHOD OF SELECTING OPERATION OF A FLUID-BED REACTOR AND APPARATUS FOR DOING SO

BACKGROUND OF THE INVENTION

The commercial advantage of the fluid-bed reactor is the ability of a fluidized-solid bed to approach isothermal conditions. This makes it possible to control the temperature closely, which in turn permits close control of the process. Though there are fluid-bed processes in which no reaction takes place, this invention is concerned only with commercial processes where a chemical reaction occurs at elevated temperature and pressure, which processes we have found, are unexpectedly correlatable in operation with a laboratory fluid-bed process operating at ambient pressure. More particularly, this invention is related to those processes using chemical reactions in fluid-bed catalysts which, we have also found, display a peculiar phenomenon best described as "tackiness" or "stickiness" which is not necessarily viscosity, as conventionally defined. Stickiness maybe defined as the degree of particle-to-particle agglomeration, viscosity or resistance to movement or separation of constituent particles. Stickiness of a support catalyst is dependent upon the pressure and temperature of the catalytic reaction, the adsorptive quality of the catalyst, the amount and distribution of active ingredient on the surface, the number of active sites available on the catalyst and the manner and degree of their utilization, and the quantity and physico-chemical properties of the reactants and reaction products in the fluid-bed.

It will be appreciated that fluid-bed catalysts, such as are used in commercial reactors in chemical processes, consist essentially of an attrition-resistant, usually porous catalyst support on which is deposited one or more essential catalytic ingredients. A typical catalyst support is silica, kieselguhr, fuller's earth, pumice, and alumina, the last named being generally preferred because of its superior resistance to attrition, its ability to fluidize and especially because it can be prepared with a desired surface area, and in a preselected ratio of particle sizes. Except for a change in color and surface area, depositing a desirable catalytic ingredient on the catalyst support does not substantially change the physical characteristics of the catalyst support, which closely resembles fine sand. In the normal course of a conventional start-up of a fluid-bed reactor, the fluid-bed catalyst gives no indication that it might undergo a change in "consistency", however this may be defined. But at elevated temperatures above about 100° C. but below a temperature deleterious to the catalyst, particularly while the catalyst is catalyzing a reaction between feed components fed to the reactor, primary particles of some catalysts exhibit a proclivity to stick to one and another, thus displaying an overall change of fluid-bed consistency within the reactor. Catalysts which exhibit such a tendency include catalyst supports on which are deposited the "soft" elements of Groups I, V, VI and VIII of the Periodic Table, and compounds thereof. Most susceptible to a change in consistency are supported catalysts on which are deposited compounds of copper, iron, bismuth, antimony and the like, and which additionally may be promoted by the rare earth elements and elements of Groups II, IV, and VII. Numerous chemical processes utilizing supported catalysts in a fluid-bed reaction are listed in the chapter entitled "Fluidization" in Encyclopedia of Chemical Technology, Kirk-Othmer, Vol. 9, p 400–404, 2d Edition, Interscience Publishers, John Wiley & Sons, Inc. (1966). Many of these catalysts are stickiness-prone during operation of the fluid-bed reactor containing the catalyst.

In specific processes listed in Kirk-Othmer (supra), such as the ammoxidation of propylene to make acrylonitrile, the oxidation of propylene to make acrolein, the oxyhydrochlorination of lower alkanes and alkanes having from 1 to 4 carbon atoms, and particularly methane to make carbon tetrachloride, chloroform, etc., and the oxyhydrochlorination of ethylene to make 1,2-dichloroethane (referred to as "EDC"), close control of these reactors is conventionally exercized by monitoring flow rates and temperatures of feed components, the pressure drop and temperature profile in the fluid-bed, reactor effluent analyses, heat duty of condensers, and the like. To obtain a good indication of what is widely believed to be the precise condition of an operating fluid bed, it is conventional to monitor the bed height, corresponding bed density and pressure drop continuously across the bed, and to record an hourly (or half-hourly) moving average bed height, bed density and pressure drop. With due experience, by correlating bed height and pressure drop with efficiency, one may continually estimate efficiency of the overall reaction. By "efficiency" we refer to conversion of one or more feed components to desirable products at mimimum cost. Desired operating conditions for a reactor (referred to in the plant as "normal optimum" operating conditions) are those which provide maximum conversion of one or more feed components to desirable products at mimimum cost. However, despite frequent pressure drop and bed height measurements derived from just-elapsed conditions, the estimate of efficiency is relatively long term, and of no value to predict an impending process "upset", whatever its cause. There is no direct correlation between bed height and the inversion point for the bed. Moreover, especially in a large operating fluid-bed reactor, any warning related to a process upset attributable to a dangerous change in bed height or a change in pressure drop is usually measured much too late to correct the conditions which gave rise to the process upset.

The importance of time will be more readily recognized when it is realized that a large fluid-bed reactor, operating at desired operating conditions has little latitude in acceptable process conditions. Moreover, in an operating fluid-bed having a quantum of stickiness, typical for a particular supported catalyst, we have found that a process upset can change the stickiness quite suddenly, long before an alarming change in pressure drop is measured. When the change in pressure drop is registered, even drastic changes in process conditions fail to restore the fluid-bed to its pre-upset operating stability. Very soon there is no alternative but to shut the reactor down. Stated differently, we have found that a process upset which causes a sudden change in stickiness of a fluid-bed operating at desired conditions, presages a process "point-of-no-return" or the "inversion point" for the fluid-bed, without immediately and significantly altering the pressure drop across the reactor. If one waits for the alarm to be set of by a sudden rise in pressure drop, or sudden collapse of the bed, it is too late. The reactor is soon shut down.

It will now be evident that, in an operating commercial fluid-bed reactor using a supported catalyst having a proclivity to increase in stickiness as conversion of reactants to a desired product improves, the risks attendant operation of the reactor at peak efficiency, near the inversion point of the fluid-bed, are too great. As a result, such a reactor is operated well short of peak efficiency with concomitant higher costs for feed components and operation of the recovery and purification systems. Pressure drop across the fluid-bed, the height of the fluid-bed, and the composition of the effluent, may all be monitored to control overall efficiency. If the fluid-bed is upset by process conditions which place the fluid-bed beyond the inversion point, the reactor is soon shut down. Though it is self-evident that the inversion point of a fluid-bed may be determined by running the bed at conditions from which there is no recovery, there is no reliable way of estimating when that inversion point may be reached under different process conditions with a particular catalyst, or with a different catalyst at the same process conditions. Measurement of changes in pressure drop by itself, is not generally correlatable with changes in stickiness. In some processes, for example in the oxyhydrochlorination of ethylene to produce EDC, pressure drop is actually found to decrease across the bed while the stickiness increases. Of course, once the inversion point is exceeded, the pressure drop will increase until the bed solidifies. There is no reason to expect that a supported catalyst should exhibit a proclivity to increase in stickiness as conversion of reactants to a desired product improves, or that the inversion point of a fluid-bed is immediately preceded by a sudden rise in stickiness, but it is, and the process of this invention is based on this finding.

It has been suggested to measure a "pseudoviscosity" or stickiness which might be a fundamental correlant of slugging, good fluidity or other bed characteristics (see Matheson, G. C., Herbst, W. A. and Holt, P.H., *Ind. Eng. Chem.* 41, 1099 (1949)). It has not be suggested that by frequently monitoring the relative pseudo-viscosity, stickiness, tackiness or consistency (all of which terms are hereafter referred to simply as "viscosity", for brevity) of an operation fluid-bed in which a chemical reaction takes place, the data might be used to maximize efficiency of the reaction; nor that a sudden rise in "viscosity", relative to the viscosity at usual operating conditions, might signal a danger-point requiring immediate attention. Neither has it been suggested that the viscosity characteristics of supported catalyst in a laboratory fluid-bed reactor operating at atmospheric pressure, may be correlateable with those of a commercial or plant fluid bed reactor operating at elevated pressure.

Recognizing that a fluid-bed displays "viscosity", a pendulum viscometer having damped torsional oscillation has been used to make measurements which are empirically correlatable to obtain a rate of damping (see "Viscometers Having Damped Torsional Oscillation", by Ashwin, B. S., Hagyard, T., et al J. Scientific Instruments, 37, p 480-485, December 1960). However, the reference is unconcerned with a reactor and does not suggest that flow rates are relatively insignificant in comparison with the reaction conditions, or change in particle size due to agglomeration induced by changes in reaction conditions. It is known that reliable rates of damping cannot be obtained with vibrating-reed type viscometers, or viscometers having quite small clearances, as in the capillary flow and the concentric cylinder type, all of which are unsuited for the purpose.

Similarly, powered viscometers in which the power to maintain a predetermined rotation is measured, are unsuited in a fluid-bed reactor because there is too much disturbance of the particles in the immediate vicinity of the viscometer. It is essential that the rate of damping be measured reliably and reproducibly, and to our knowledge, this can only be done with a pendulum viscometer which uses relatively low rotational velocity, and which does not appreciably disturb the state of the fluid bed in the immediate vicinity of the viscometer.

SUMMARY OF THE INVENTION

It has been discovered that a relationship exists between the viscosity of an operating fluid-bed near its inversion point (which viscosity is referred to hereinafter as "peak viscosity", for brevity), and its viscosity at desired operating conditions at which a reactor is usually run (hence referred to herein as "usual viscosity"), a change in which relationship may be used to signal a process upset requiring immediate correction.

It is therefore a general object of this invention to provide a method for obtaining desired operation of a fluid-bed reactor provided with a pendulum viscometer, and means to provide the pendulum with a preselected initial angular displacement, comprising: (a) charging said reactor with a supported catalyst in the presence of which a chemical reaction occurs which increases stickiness of said catalyst as conversion to desired products improves, (b) measuring a peak rate of damping of a predetermined torsional oscillation of said pendulum during operation of said fluid-bed at or near its inversion point, (c), measuring a usual rate of damping of said predetermined torsional oscillation of said pendulum during desired operating conditions, (d) obtaining a quantitative difference between said usual rate and said peak rate of damping, and (e) adjusting said process conditions to operate said reactor while maintaining approximately said quantitative difference. By "desired operating conditions" we refer to the most preferred operation of the reactor, often referred to as the optimum normal operating conditions, at which maximum conversion to desired products is obtained at minimum cost.

It has also been discovered that, though operating at ambient pressure, a laboratory fluid-bed reactor equipped with a torsional pendulum and related auxiliary means for measuring and recording the rate of damping of the pendulum, may be used to reproduce the effects of the viscosity variations in the fluid-bed of a pressurized commercial reactor.

It is therefore a general object of this invention to provide a laboratory apparatus for measuring the relative viscosity of a normally operating fluid-bed of supported catalyst with a pendulum viscometer having damped torsional oscillations comprising, means for creating a fluctuating electrical potential proportional to the angular displacement of the pendulum during each successive oscillation, means for rectifying said potential to produce a unidirectional potential having amplitudes proportional to said displacement, means for recording the output of said rectifying means, and means for recording the slope of said output.

BRIEF DESCRIPTION OF THE DRAWINGS

The invention in its several aspects, including other objects, features and advantages not above mentioned, will be more fully understood by now referring to the following detailed description of a preferred embodiment thereof, reference for this purpose being had to the accompanying drawing, in which.

DETAILED DESCRIPTION OF PREFERRED EMBODIMENTS OF THE INVENTION

Figure 1:
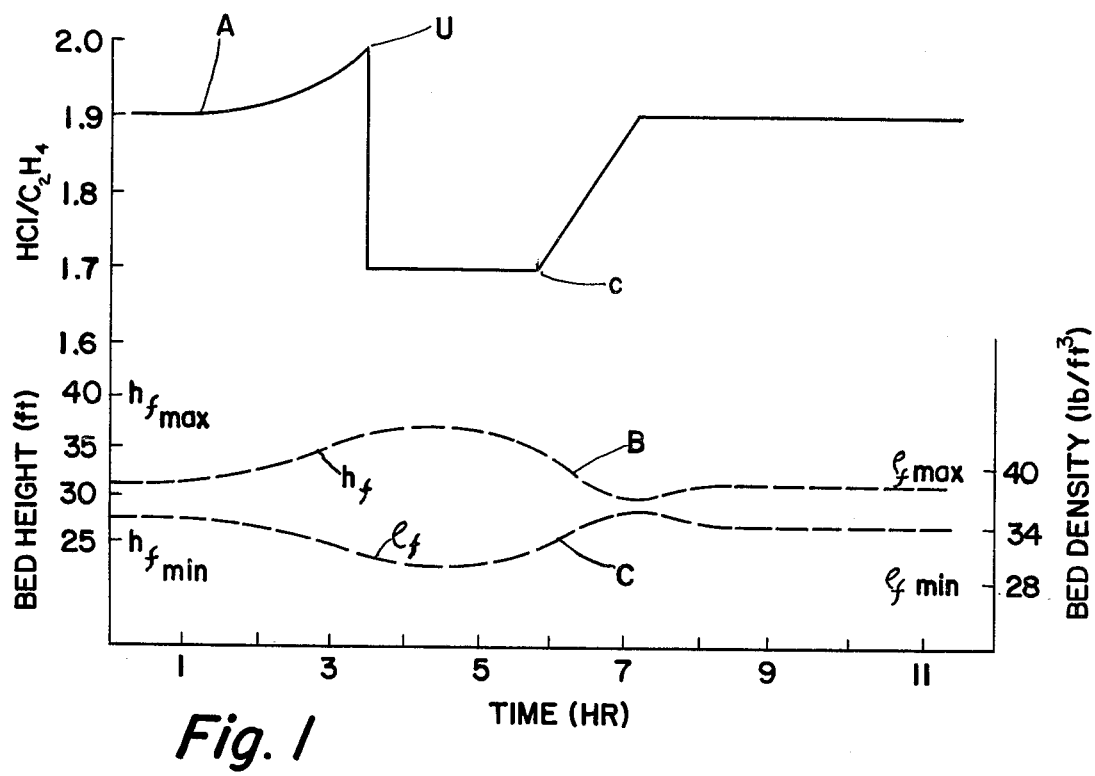
FIG. 1 is a graphical simulation of the effect of a typical process upset in the oxyhydrochlorination of ethylene to EDC in a fluid-bed reactor, as evidenced by measurements of the ratio of feed components, particularly HCL:$C_2H_4$, bed height and corresponding bed density, all plotted as a function of time.

The apparatus of this invention is a laboratory fluid-bed reactor and includes related auxiliary equipment to measure and record the viscosity characteristics of an operating fluid-bed. The pressure within the reactor is essentially atmospheric. By "viscosity" we particularly refer to a characteristic stickiness peculiar to certain supported catalysts which have deposited thereon at least one essential catalytic ingredient consisting essentially of at least one element, or an inorganic compound of an element, selected from Groups I B, III B, V B and VI of the Periodic Table optionally combined with a promoter selected from the group consisting of elements and compound of elements of Groups II, VII, and VIII. The catalytic ingredients of Groups I B, III B, V A and VI A are generally referred to as being "soft" because of their propensity to imbue a catalyst support on which they are deposited, with a peculiar stickiness, referred to herein as "viscosity". This viscosity increases progressively as the efficiency of a fluid-bed of the supported catalyst approaches theoretical maximum for selected operating conditions. Specific active ingredients which display this progressive increase in viscosity of a fluid-bed approaching optimum operating conditions, are the compounds of copper, silver, bismuth, phosphorus, antimony, and uranium. The apparatus may be used to measure the relative viscosity characteristics of any single fluent material, or a mixture of materials, but as will presently be apparent, has particular utility for the measurement of viscosity characteristics of a fluid-bed while in operation.

The method of this invention is useful to correlate the operation of a pressurized commercial or "plant" reactor, with an unpressurized laboratory reactor in which the process conditions of the plant reactor are simulated for feed ratios, contact time and temperature, but not for pressure. The laboratory reactor is operated concurrently with the plant reactor, simulating the plant reactor's operating conditions, but ignoring pressure. Any change in process conditions in the plant reactor is simulated in the laboratory reactor, where the effect upon viscosity is quickly evidenced as a change in the value of the decay constant before it is evidenced as a change in pressure drop, bed height or bed density, and before an effluent analysis from the plant reactor would indicate that a process upset has occurred. The necessary process adjustments are made to return the laboratory reactor to normal operation, near the optimum, and the appropriate analogous process adjustments are then made in the plant reactor though it (the plant reactor) provides no evidence that such changes are necessary. Thus, the effects of the process upset are minimized, and desired reactor operating conditions are maintained.

The method of this invention is also useful to select the most desirable catalyst from a number of catalysts with slightly varying specifications, or even from several batches of purportedly identical catalysts, by performance testing them with the fluid-bed viscometer of this invention. On the basis of performance, one can then select the catalyst which produces highest yields, yet displays the least sensitivity to process upsets. It will be appreciated that such testing by actual performance, will foreseeably include the testing from time to time, of "used" catalyst, that is catalyst still in use in the plant reactor, to determine whether its sensitivity and/or its efficiency has been impaired.

A preferred embodiment of the method of this invention will be described as it applies to the operation of a catalytic fluid-bed process in which ethylene is reacted with oxygen and hydrogen chloride in the presence of a copper chloride supported catalyst, to produce 1,2-dichloroethane ("EDC"). In this oxyhydrochlorination process, the catalyst is preferably cupric chloride supported on an attrition resistant catalyst support such as silica, kieselguhr, clay and alumina, alumina being preferred. The process is described in detail in U.S. Pat. No. 3,488,398 the disclosure of which is incorporated by reference thereto as if fully set forth herein.

The overall reaction for converting ethylene to 1,2-dichloroethane can be written empirically as follows:

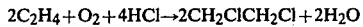

$$2C_2H_4 + O_2 + 4HCl \rightarrow 2CH_2ClCH_2Cl + 2H_2O$$

During the reaction some $C_2H_4$ is converted to higher chloride containing materials and some is oxidized to CO and $CO_2$, so it is desirable to use a slight excess of $C_2H_4$ and $O_2$ over stoichiometric. Thus, for every two moles of HCl, from about 1.02 to about 1.2 moles of $C_2H_4$, and from about 0.55 to about 0.9 mole of $O_2$ are preferably fed into the reactor to maximize utilization of HCl. The most preferred molar ratio of ethylene, HCl and oxygen is 1:1.9:0.8. Preheated feed components are contacted with the catalyst after it is fluidized and maintained at a temperature in the range from about 210° C. to about 240° C., in a plant reactor pressurized in the range from about 10 to 100 psig. It is essential that a bare minimum of excess HCl be fed to the reactor, and that the maximum conversion of ethylene be obtained, both from the standpoint of effective use of the reactants as well as from the standpoint of minimizing the corrosive effects and purification problems in the recovery system. The catalyst is prepared by impregnating microspheroidal gel alumina with a solution of copper chloride, and drying it so that the amount of copper salt on the support is in the range from about 2.0 to about 12% by weight copper.

In a typical operation of the plant reactor, the ratio of HCl to ethylene is monitored, along with the bed height and the bed density. It is desirable to maintain each within a narrow range in which operation of the reactor is known to be safe. A process upset is evidenced when the bed height increases (say) beyond its preferred prescribed boundary, and the bed density decreases correspondingly. To mitigate the effect of a mushrooming process upset, the ratio of HCl:ethylene is immediately changed (decreased), by increasing the flow of $C_2H_4$, but overcompensated to ensure that both the bed height and density revert to values within prescribed operating limits. The overcompensation, and subsequent compensating attempts to return the bed to a stable, safe and cost-effective operating condition, may be made over several operating shifts and a period of days during most of which period the reactor is operating at process conditions which may be safe but far from the desired operating conditions.

Referring now to FIG. 1 there is shown a graph for a typical upset in a large plant reactor, in which graph is plotted (a) ratio of HCL: $C_2H_4$ (Curve A); (b) bed height, $h_f$(Curve B); and, (c) bed density, $\rho_f$(Curve C); all as a function of time. Operating limits for each are indicated on the graph with subscripts "max" and "min."

Referring first to Curve A, the ratio 2 is the upper (stoichiometric) limit at which operation for any substantial length of time will result in exceeding the inversion point. At the lower limit of 1.6, excessive use of ethylene results with incidental problems in recovery and purification. The most preferred usual operating ratio for the EDC process is about 1.9, the precise ratio being affected by the supported catalyst used, the variations in concentration of components which make-up the feed stream, the actual geometry of the fluid-bed reactor, and other physical considerations.

Referring now to Curve B, the bed height may vary within relatively narrow limits, about ±20% from the usual operating bed height at the usual operating ratio (1.9) of $HCl/C_2H_4$. As shown in Curve B, a bed usually operating at a height of 31 ft may increase in height to about 37 ft during a process upset, and then decrease to about 31 ft after a correction in ratio is made. Referring to Curve C, the bed density during operation may vary within minimum and maximum limits from about 28 lb/ft$^3$, marked $\rho_{fmin}$ on the right hand side of FIG. 1, to about 40 lb/ft$^3$. During a process upset, the bed density may vary about ±20% from the usual operating density.

A bed condition where maximum bed density and maximum pressure drop are simultaneously exceeded indicates that the inversion point (not shown in this Figure) has been reached. Essentially parallel lines, for each of the variables being plotted, near the beginning of the time period indicates stable operation of the reactor at desired operating conditions. The first increase in the ratio of HCl: $C_2H_4$ occurs from about 1.9 to about 1.98, which as shown occurs gradually, but may also occur suddenly. The increase indicates a process upset which is corrected at the point indicated by reference symbol U, by increasing the flow of ethylene sufficiently to lower the ratio to about 1.7. Despite the increase of mass flow of gases to the reactor, the bed height $h_f$ which initially increased as the ratio of HCl: $C_2H_4$ increased, begins to level off as does, correspondingly, the bed density. After a period of time the bed height commences to fall and, correspondingly, the bed density increases though the ratio is maintained at 1.7. When the rate of decrease of bed height, and correspondingly, the rate of increase of density, as is evidenced by the slopes of the curves, appears to accelerate, a correction of the ratio is made at the point indicated by the reference symbol "c", by slowly decreasing the rate of flow of $C_2H_4$ and increasing the ratio to about 1.9 (say). Having thus reverted to the initial ratio at which desired operating conditions are attained, it is hoped that stable conditions, as illustrated by the parallel lines after point C, become re-established. Several additional corrections may be necessary before the desired operating corrections are achieved. At no time during which the ratio, pressure drop and bed height (or density) are unstable is there evidence of how closely the inversion point was approached, if indeed it was apaproached at all. The evidence indicates that the bed suffered a process upset which was countered by correcting the HCL: $C_2H_4$ ratio at point U; that after a period of time, the rates of change of bed height and density indicated that there was an overcorrection which was again countered by correcting the ratio at point C; and, that thereafter the initial, stable desired operating conditions became re-established. The evidence does not indicate where the optimum operating conditions existed, or whether they existed at all.

Figure 2:
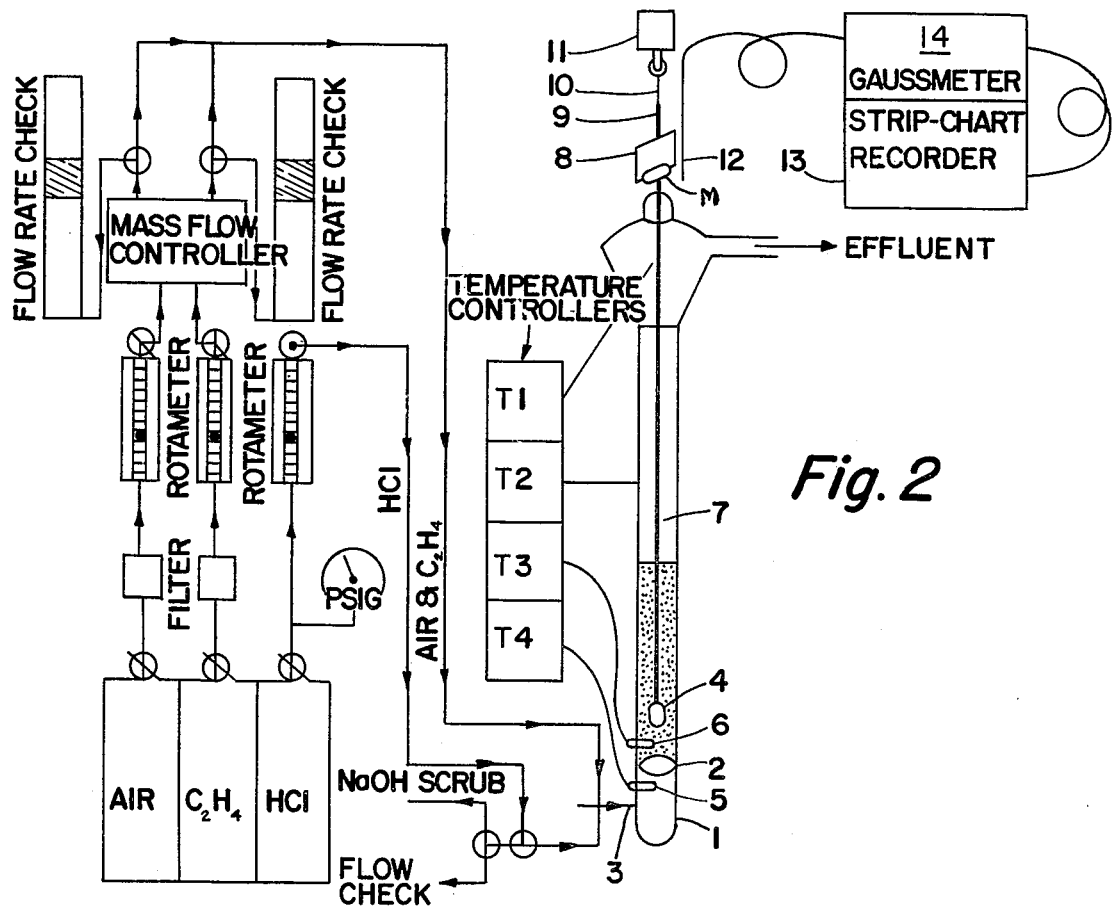
FIG. 2 is a schematic illustration of a laboratory fluid-bed reactor in which a catalytic reaction is carried out. The reactor is fitted with a pendulum viscometer and is provided with related auxiliary measuring means for measuring and recording viscosity of the fluid-bed during operation.

Simulation of the operation of a plant reactor will be more readily understood by reference to FIG. 2 wherein a laboratory reactor is diagrammatically illustrated, identified generally by reference numeral 1, including a glass tube about 2" in diameter and about 3.5 ft long, in which is placed a bed of supported cupric chloride catalyst resting on a gas-permeable porous glass frit, or sintered metal plate 2. The glass tube reactor has an enlarged upper end from which, at a point marked EFFLUENT, the effluent is ducted for analysis and recovery (not shown). Thermocouple wells 5 and 6 are provided above and below the porous plate 2, and several thermocouples are connected to a bank of temperature controllers T1, T2, T3 and T4. Air, ethylene and anhydrous HCl are flow controlled by conventional means illustrated, and mixed just prior to being introduced into the reactor, near its bottom, through feed line 3. A pendulum is longitudinally axially disposed within the reactor 1, its bob 4 being immersed in the bed of catalyst. The bob 4 is affixed to one end of a rigid rod 7, the other end of which protrudes from the top of the reactor. A permanent magnet M is removably affixed to said other end of the rod 7 so that the magnet is symmetrically disposed about the longitudinal axis of the rod. A rectangular frame 8 is provided to facilitate mounting of the magnet. A short extension of rigid rod 9 extends from the frame 8, the extension 9 being longitudinally axially aligned with the rod 7, and forming with the frame 8, a rigid assembly. The pendulum this includes extension 9, the magnet M in its frame 8, the rod 7 and the bob 4. The pendulum is suspended from an actuator means 11 by a torsion wire 10.

The actuator means 11 serves to provide a sudden predetermined angular torque to the torsion wire 10 which transmits the torque to the pendulum. This function is conveniently provided by a modified air operated ball valve (such as is commercially available from the Whitey Co., Oakland, California), in which the valve has been removed but the valve stem retained, so that the stem is pneumatically actuatable and rotatable through a predetermined angle, preferably in the range from about 5° to about 40°. After actuation and subsequent damping, the stem is returned to its original position by a spring. it is preferred to air-actuate the actuator 11 at regular intervals by a solenoid which is energized by a timing mechanism, say at intervals from about 30 secs to about 15 min, not including the period of damping of the pendulum. Details of the actuator mechanism are not shown as they are well-known. Also the precise manner in which the actuation is imparted to the pendulum is not critical, it only being important that the sudden torque, through a predetermined angle, be reliably and reproducibly imparted to the pendulum.

Adjacent the magnet M and in magnetic communication therewith is placed a Hall probe 12 in which is generated a fluctuating electrical potential induced by the oscillating magnetic field of the magnet. Current from the Hall probe is conducted to a gaussmeter 14, and thence, part to a strip chart recorder 13 and part to a computer (not shown), popularly referred to as a "peak picker," which reads the peaks of the signals from the gaussmeter, where the signals are appropriately amplified, as is well-known in the art. Amplitudes of successive oscillations of the pendulum, after it is given an initial angular displacement when the actuator means is air-actuated, are recorded on either the positive (preferred) or negative side of the horizontal. The slope of the curve formed by joining the peak points is computed to obtain a decay constant for the damped harmonic oscillations of the pendulum, which oscillations decay exponentially with time. The decay constant so obtained is directly proportional to the viscosity of the fluid bed of catalyst in the reactor.

Figure 3:
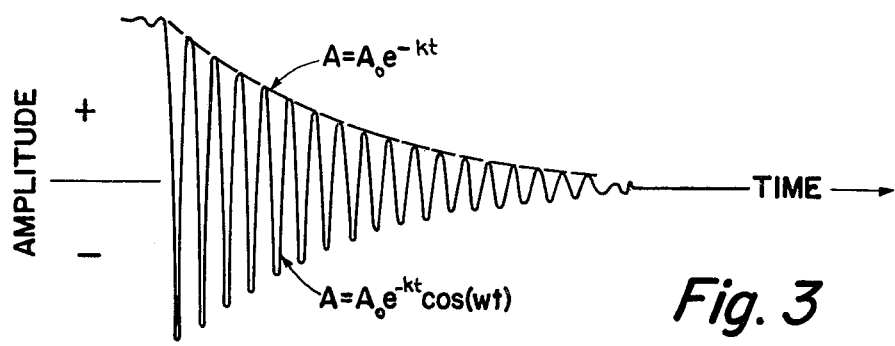
FIG. 3 is a reproduction of a representative strip chart graphically illustrating a fluctuating output signal of diminishing amplitude.

The foregoing may be stated mathematically as follows:

$$A = A_o e^{-kt} \cos(\omega t)$$

where
A = amplitude of detector response
$\omega$ = angular frequency
t = time
k = exponential decay constant Referring now to FIG. 3 there is illustrated a representative strip chart graphically illustrating a fluctuating output signal of diminishing amplitude. The curve, shown as a dotted line, connecting the peaks on the positive side of the horizontal, may be defined by the equation:

$$A = A_o e^{-kt}$$

because frequency remains constant, from which $$\ln A = -kt + \ln A_o$$

Figure 4:
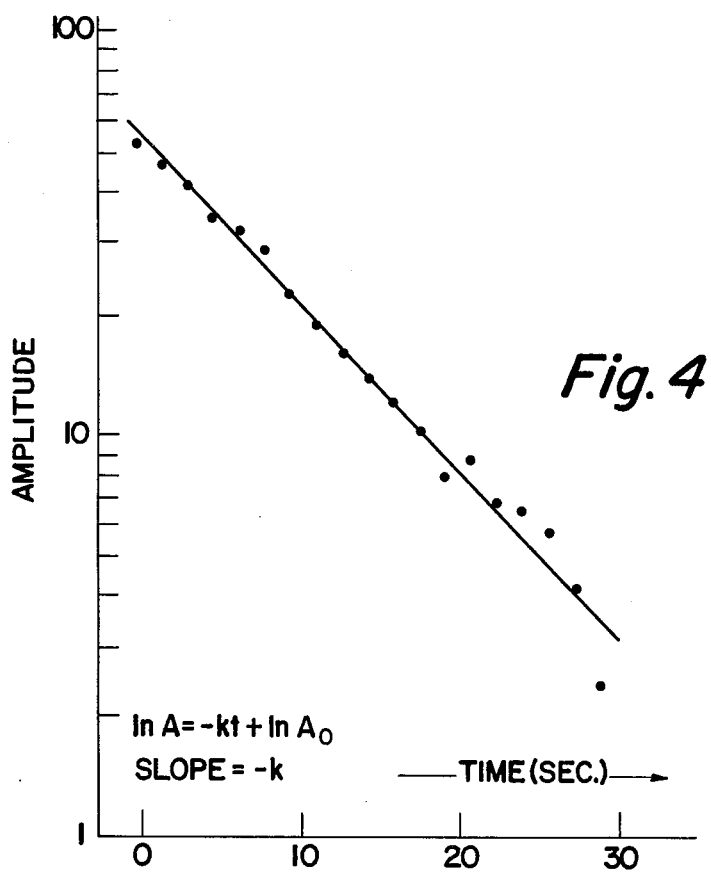
FIG. 4 is a semilog plot graphically illustrating successively diminishing peak amplitudes corresponding to damped torsional oscillations as a function of time.

Referring now to FIG. 4 there is illustrated a semilog plot graphically illustrating successively diminishing peak amplitudes corresponding to damped torsional oscillations as a function of time. The scale for amplitude is set arbitrarily, the first amplitude being the greatest, and successive amplitudes diminishing over a period about 30 secs. The initial amplitude will be determined by the apparatus. The period over which damping occurs will be determined by bed characteristics. The slope is quantitatively defined by "k," relative values of which are a measure of the relative stickiness of the catalyst.

Figure 5:
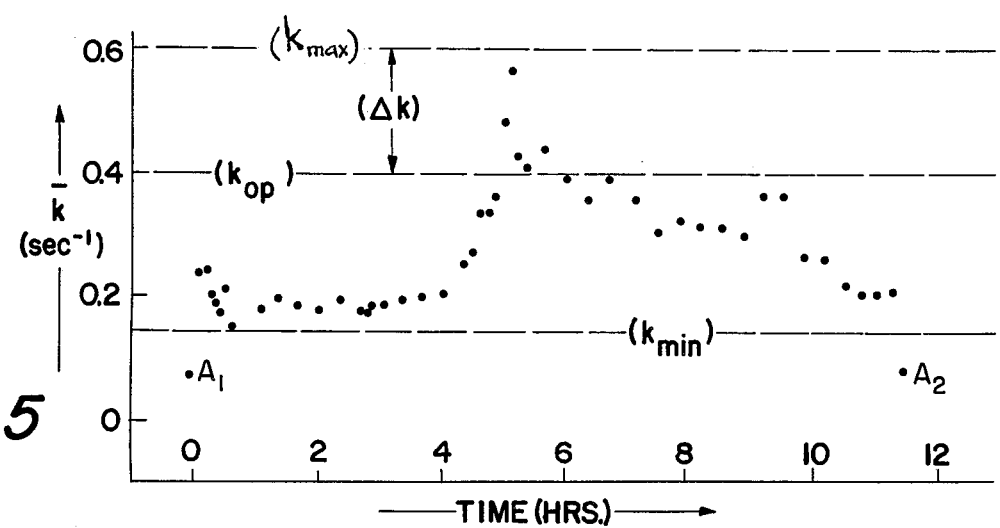
FIG. 5 is a plot graphically illustrating the rate of damping with time, and the recovery of the fluid-bed from a process upset near the "inversion point", but before a sharp pressure drop across the bed could be measured.

Referring now to FIG. 5 there is illustrated a plot of the rate of damping as a function of time. The dotted horizontal line through a point marked $k_{min}$ indicates stable but inefficient operation of the fluid bed. The dotted horizontal line through a point marked $k_{max}$ indicates maximum stickiness at or near the inversion point. The dotted horizontal line through a point marked $k_{op}$ indicates usual stickiness, at desired operating conditions, at which desired efficiency of the reaction is obtained. The numerical quantitative difference $\Delta k$ between $k_{op}$ and $k_{max}$ is the desired difference between the stickiness as evidenced by the usual rate of damping ($k_{op}$) and the peak rate of damping ($k_{max}$).

Dots in FIG. 5 represent the average of 5 values of k (represented as $\bar{k}$) on a series of sets of readings (five readings for each set), each reading made at intervals about 1 minute. With the particular system for which the measurements plotted as dots in FIG. 5 were made, that is, with a particular pendulum, angular displacement, fluid-bed laboratory reactor, catalyst, and process conditions, the inversion point occurred near $k = 0.6$. The operating range for the reactor is in the range from $k = 0.15$ for a lower limit, to just above about $k = 0.4$, which is a desired operating upper limit, i.e. an operating range from about 25% to about 67% of $k_{max}$. It will now be evident that operation of the fluid-bed reactor at values of k near the lower limit will provide safer operation but lower efficiency while operating values of k near the upper limit provide greater efficiency but less margin of safety. In general, a ratio of $HCl:C_2H_4$ of about 1.9 allows operation near the upper operating limit of k, i.e. near 67% of $k_{max}$, though these values may vary from one catalyst to another.

Of particular interest are values of $\bar{k}$ which are represented by dots $A_1$ and $A_2$ on FIG. 5. Prior to commencing the oxyhydrochlorination reaction on the supported copper chloride catalyst, the bed is fluidized with only that amount of air corresponding to 0.8 moles oxygen per mole of ethylene to be fed for the reaction at reactor operating temperature. The value of $\bar{k}$ (average for 5 readings) is represented by $A_1$ and is about 0.13. Thereafter ethylene and HCl are also fed to the reactor nearly doubling the mass flow of gases through the fluid-bed, and decreasing the bed density, yet the value of $\bar{k}$ increases. After numerous sets of readings are made for various ratios of $HCl:C_2H_4$, the $\bar{k}$ values for which are represented by the dots in FIG. 5, the flow of both HCl and $C_2H_4$ is discontinued, and a set of 5 readings are taken with only air being flowed to the reactor. The average of this set of 5 readings is represented by the dot identified as $A_2$ and is about 0.13, which indicates that without the chemical reaction, the viscosity of the fluid-bed with air flow only, is essentially constant.

The method described hereinabove, of selecting a desirable mode of operation of a fluid-bed reactor, and the apparatus for doing so, may be adapted, with appropriate engineering modifications, to a commercial reactor in which the pendulum viscometer is disposed inside the reactor, so as to provide direct readings of viscosity while the reactor is operating. In such an embodiment it is possible to be informed, essentially continuously, of the condition of the catalyst in the reactor as well as the efficiency of the reaction therewithin.

We claim:

1. In a process for the ammoxidation of a monoolefin having 3 or 4 carbon atoms, using a catalytic fluid-bed reactor in which ammonia, oxygen and said monoolefin are feed components, which reactor is provided with a pendulum viscometer with low rotational velocity which does not appreciably disturb the state of said fluid-bed in the immediate vicinity of said viscometer, and means to provide said pendulum with a preselected initial angular displacement, a method for obtaining desired operation of said reactor comprising, (a) charging said reactor with a supported catalyst on which is deposited at least one element selected from the group consisting of elements of Groups I, V, VI and VIII of the Periodic Table and compounds thereof, in the presence of which supported catalyst said ammoxidation occurs which increases stickiness of said catalyst as conversion of said feed components to desired products is improved, (b) operating said reactor at an elevated temperature above about 100° C. but below a temperature deleterious to said catalyst, (c) measuring a peak rate of damping of a predetermined torsional oscillation of said pendulum viscometer during operation of said fluid-bed at or near its inversion point, (d) measuring a usual rate of damping of said predetermined torsional oscillation of said pendulum viscometer during usual, desired operating conditions, (e) obtaining a quantitative difference between said usual rate and said peak rate of damping, and (f) adjusting process conditions to operate said reactor while maintaining approximately said quantitative difference.

2. The process of claim 1 wherein said reaction occurs at or above about atmospheric pressure.

3. The process of claim 2 wherein said quantitative difference is obtained at predetermined intervals of time, at least once every 8 hours during operation of said reactor.

4. The process of claim 3 wherein said supported catalyst is additionally promoted by an element selected from the group consisting of rare earth elements and an element of groups II, IV, and VII of the Periodic Table.

5. The process of claim 4 wherein said monoolefin is propylene.

6. In a process for the oxyhydrochlorination of a monoolefin having from 2 to about 4 carbon atoms, using a catalytic fluid-bed reactor in which hydrochloric acid, oxygen and said monoolefin are feed components, which reactor is provided with a pendulum viscometer with low rotational velocity which does not appreciably disturb the state of said fluid-bed in the immediate vicinity of said viscometer, and means to provide said pendulum with a preselected initial angular displacement, a method for obtaining desired operation of said reactor comprising, (a) charging said reactor with a supported catalyst on which is deposited at least one element selected from the group consisting of elements of Groups I, V, VI and VIII of the Periodic Table and compounds thereof, in the presence of which supported catalyst said oxyhydrochlorination occurs which increases stickiness of said catalyst as conversion of said feed components to desired products is improved.

(b) operating said reactor at an elevated temperature above about 100° C. but below a temperature deleterious to said catalyst, (c) measuring a peak rate of damping of a predetermined torsional oscillation of said pendulum viscometer during operation of said fluid-bed at or near its inversion point, (d) measuring a usual rate of damping of said predetermined torsional oscillation of said pendulum viscometer during usual, desired operation conditions, (e) obtaining a quantitative difference between said usual rate and said peak rate of damping, and (f) adjusting process conditions to operate said reactor while maintaining approximately said quantitative difference.

7. The process of claim 6 wherein said reactor occurs at or above about atmospheric pressure.

8. The process of claim 7 wherein said quantitative difference is obtained at predetermined intervals of time, at least once every 8 hours during operation of said reactor.

9. The process of claim 8 wherein said supported catalyst is additionally promoted by an element selected from the group consisting of rare earth elements and an element of groups II, IV, and VII of the Periodic Table.

10. The process of claim 8 wherein said monoolefin is ethylene, said reactor is charged with a supported copper chloride catalyst and is operated at a temperature in the range from about 200° C. to about 300° C.

11. In a process for the oxidation of a monoolefin having 3 or 4 carbon atoms, using a catalytic fluid-bed reactor in which oxygen and said monoolefin are feed components, which reactor is provided with a pendulum viscometer with low rotational velocity which does not appreciably disturb the state of said fluid-bed in the immediate vicinity of said viscometer, and means to provide said pendulum with a preselected initial angular displacement, a method for producing an unsaturated aldehyde while obtaining desired operation of said reactor comprising, (a) charging said reactor with a supported catalyst on which is deposited at least one element selected from the group consisting of elements of Groups I, V, VI and VIII of the Periodic Table and compounds thereof, in the presence of which supported catalyst said oxidation occurs which increases stickiness of said catalyst as conversion of said feed components to desired products is improved, (b) operating said reactor at an elevated temperature above about 100° C. but below a temperature deleterious to said catalyst, (c) measuring a peak rate of damping of a predetermined torsional oscillation of said pendulum viscometer during operation of said fluid-bed at or near its inversion point, (d) measuring a usual rate of damping of said predetermined torsional oscillation of said pendulum viscometer during usual, desired operating conditions, (e) obtaining a quantitative difference between said usual rate and said peak rate of damping, and (f) adjusting process conditions to operate said reactor while maintaining approximately said quantitative difference.

12. The process of claim 11 wherein said reaction occurs at or above about atmospheric pressure.

13. The process of claim 12 wherein said quantitative difference is obtained at predetermined intervals of time, at least once every 8 hours during operation of said reactor.

14. The process of claim 13 wherein said supported catalyst is additionally promoted by an element selected from the group consisting of rare earth elements and an element of groups II, IV, and VII of the Periodic Table.

15. The process of claim 14 wherein said monoolefin is propylene.

16. In a process for the oxyhydrochlorination of an alkane having from 1 to about 4 carbon atoms, using a catalytic fluid-bed reactor in which hydrochloric acid, oxygen and said alkane are feed components, whch reactor is provided with a pendulum viscometer with low rotational velocity which does not appreciably disturb the state of said fluid-bed in the immediate vicinity of said viscometer, and means to provide said pendulum with a preselected initial angular displacement, a method for obtaining desired operation of said reactor comprising, (a) charging said reactor with a supported catalyst on which is deposited at least one element selected from the group consisting of elements of Groups I, V, VI and VIII of the Periodic Table and compounds thereof, in the presence of which supported catalyst said oxydrochlorination occurs which increases stickiness of said catalyst as conversion of said feed components to desired products is improved, (b) operating said reactor at an elevated temperature above about 100° C. but below a temperature deleterious to said catalyst, (c) measuring a peak range of damping of a predetermined torsional oscillation of said pendulum viscometer during operation of said fluid-bed at or near its inversion point, (d) measuring a usual rate of damping of said predetermined torsional oscillation of said pendulum viscometer during usual, desired operating conditions, (e) obtaining a quantitative difference between said usual rate and said peak rate of damping, and (f) adjusting process conditions to operate said reactor while maintaining approximately said quantitative difference.

17. The process of claim 16 wherein said reaction occurs at or above about atmospheric pressure.

18. The process of claim 17 wherein said quantitative difference is obtained at predetermined intervals of time, at least once every 8 hours during operation of said reactor.

19. The process of claim 18 wherein said supported catalyst is additionally promoted by an element selected from the group consisting of rare earth elements and an element of groups II, IV, and VII of the Periodic Table.

20. The process of claim 19 wherein said alkane is methane.

* * * * *